United States Patent [19]

Knifton et al.

[11] 4,451,679

[45] * May 29, 1984

[54] ALCOHOLS AND ALDEHYDES PREPARED FROM OLEFINS AND SYNTHESIS GAS

[75] Inventors: John F. Knifton, Austin; Jiang-Jen Lin, Round Rock; Robert A. Grigsby, Jr., Georgetown; Walter H. Brader, Jr., Austin, all of Tex.

[73] Assignee: Texaco Inc., White Plains, N.Y.

[*] Notice: The portion of the term of this patent subsequent to May 29, 2001 has been disclaimed.

[21] Appl. No.: 435,812

[22] Filed: Oct. 21, 1982

[51] Int. Cl.$^3$ .............................................. C07C 27/22
[52] U.S. Cl. .................................. 568/909; 568/451; 568/454
[58] Field of Search ...................... 568/454, 451, 909

[56] References Cited

U.S. PATENT DOCUMENTS

| 3,527,809 | 9/1970 | Pruett et al. | 568/454 |
| 3,636,159 | 1/1972 | Solomon | 568/454 |
| 4,306,084 | 12/1981 | Pettit | 568/454 |
| 4,306,085 | 12/1981 | Kim et al. | 568/454 |
| 4,317,936 | 3/1982 | Kim et al. | 568/454 |

FOREIGN PATENT DOCUMENTS

| 751353 | 12/1970 | Belgium | 568/454 |
| 988943 | 7/1961 | United Kingdom | 568/454 |
| 966482 | 8/1964 | United Kingdom | 568/454 |
| 999461 | 7/1965 | United Kingdom | 568/909 |

OTHER PUBLICATIONS

Suss-Fink, "J. Organomet. Chem", 193 C20–22, (1980).
Pitman et al., "J. Org. Chem.", vol. 46, p. 1901, (1981).

Primary Examiner—Werren B. Lone
Attorney, Agent, or Firm—Robert A. Kulason; Jack H. Park; Cynthia L. Kendrick

[57] ABSTRACT

This invention concerns a process of preparing alcohols and aldehydes which comprises the steps of contacting a mixture of terminal and/or internal olefins and synthesis gas with a catalyst system comprising a ruthenium-containing compound dispersed in a low melting quaternary phosphonium or ammonium base or salt and heating said resultant reaction mixture under a pressure of 100 psi or greater at a temperature of at least 50° C. for a sufficient time to produce said alcohols and aldehydes.

28 Claims, No Drawings

ALCOHOLS AND ALDEHYDES PREPARED FROM OLEFINS AND SYNTHESIS GAS

BACKGROUND OF THE INVENTION

1. Field of the Invention

This invention concerns an improved process for preparing alcohols and aldehydes by the reaction of synthesis gas and terminal or internal olefins in the presence of a catalyst system.

2. Prior Art

The processes of hydroformylation and carbonylation are well known in the art and involve reactions represented by:

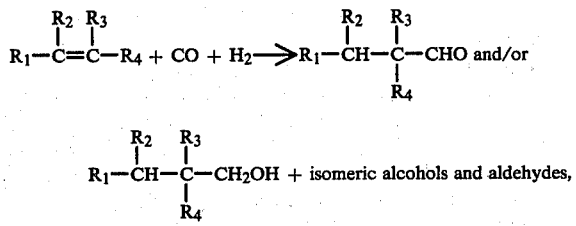

wherein the aldehydes and alcohols produced generally correspond to the compounds obtained by the addition of a carbonyl or carbinol group to an olefinically unsaturated carbon atom in the starting material with simultaneous saturation of the olefin bond. Isomerization of the olefin bond may take place to varying degress under certain conditions with consequent variation in the products obtained.

The hydroformylation reaction does not generally proceed in the absence of catalysts, and a disadvantage of many of the hydroformylation processes disclosed heretofore is their dependence upon the use of catalysts, particularly the commonly-used cobalt-derived homogenous 'oxo' catalysts, which generally necessitate the use of exceedingly high pressures to remain stable under the conditions employed. A further disadvantage of many of the processes disclosed heretofore is their inability to produce hydroformylation products comprising substantial amounts of alcohols, thereby necessitating a separate aldehyde hydrogenation step when alcohols are a desired product. The production of hydroformylation products having a relatively high normal to branched product isomer ratio is also often exceedingly difficult, if at all possible, in many of the practical scale processes now in use. Another problem in many common practiced hydroformylation processes is by-product formation on account of competing reactions. Examples of such unwanted by-products include alkanes, formed through competing olefin hydrogenation, olefin isomers formed through double bond isomerization, ketone formation and aldols generated as a result of product aldehyde condensation reactions.

In commercially practiced hydroformylation processes cobalt- and rhodium-catalyzed systems are most commonly used,[1] and while cobalt and rhodium have been the focus of much of the prior hydroformylation research, numerous other metals have been disclosed as catalysts for this synthesis.

[1] (For a review of the prior art pertaining to the use of cobalt and rhodium-based hydroformylation processes see: R. L. Pruett, "Advances in Orcanometallic Chemistry", Vol. 17, p. 1 (1979)).

Typical of the prior art relating to the use of ruthenium as a hydroformylation catalyst are the publications of Wilkinson and co-workers. In British Pat. No. 1,138,601, Example 6, the hydroformylation of alpha-olefins (1-hexene) to aldehydes is described using soluble, phosphine-stabilized ruthenium catalysis precursors, such as $[(Ph_2EtP)_6Ru_2Cl_2]Cl$. Here moderately high pressures are used and the use of a two step hydroformylation and subsequent hydrogenation step as a synthetic route to alcohols is discussed. Additional information regarding the use of a variety of tertiary-phosphine-ruthenium complexes in the catalytic hydroformylation of alkenes to aldehydes-particularly the dependence of conversion and aldehyde ratios upon catalyst concentration, temperature, partial and total pressures, nature of the substrate, and the addition of excess phosphine-may be found in a second publication by this group in J. Chem. Soc. p. 399 (1976). Similar classes of catalysts are disclosed also in U.S. Pat. No. 3,239,566, assigned to Shell Oil Company. In particular, this patent relates to the production of aldehydes and-/or alcohols by the addition of carbon monoxide and hydrogen to olefinic hydrocarbons in the presence of a catalyst consisting of a ruthenium or rhodium component in complex combination with carbon monoxide and a trialkylphosphine. Here, the greatest percentage of the converted olefins form alcohols and aldehydes with less than seven carbons.

The use of ruthenium salts, such as ruthenium(III) chloride and ruthenium stearate, as well as ruthenium carbonyls and ruthenium on carbon, as catalyst precursors for the hydroformylation of olefins to straight-chain and branched aldehydes is disclosed in British Pat. Nos. 966,461 and 999,461, assigned to Imperial Industries Limited. Pettit, in U.S. Pat. No. 4,306,084, describes an oxo process reaction where the ruthenium carbonyl catalyst is maintained in a basic solution. Recently the cluster anion, $[HRu_3(CO)_{11}]^-$, has been shown to catalyze the hydroformylation of ethylene and propylene to $C_3$-$C_4$ aldehydes in dimethylformamide at 100° C. (See. C. Suss-Fink, J. Organomet. Chem., 193, C20 (1980)).

Polymer-bound ruthenium hydroformylation catalysts, prepared, for example, by reacting diphenylphosphinated styrenedivinylbenzene resins with phosphine-stabilized ruthenium carbons, have also been described recently. Pittman, in J. Org. Chem. 46, 1901 1981), finds improved normal/branched aldehyde ratios with these resins compared with homogenous catalyst versions. The more desirable alcohol products are not reported to be formed with this class of ruthenium catalyst.

U.S. Pat. No. 3,239,569 discloses the production of aldehydes and alcohols in a single stage conversion which comprises contacting an olefinic hydrocarbon with carbon monoxide and hydrogen in the presence of a catalyst system comprising cobalt in complex combination with carbon monoxide and a trialkylphosphine. Here again, the majority of the hydroformylation products were six carbons or less.

There is then a need in the art for a one stage process of preparing alcohols and aldehydes, from olefinically unsaturated compounds, particularly internal olefin compounds, by a process which utilizes lower pressures and results in a high yield of aliphatic alcohols of the $C_8$-$C_{20}$ range.

An object of this invention, therefore, is the oxonation of olefins, particularly higher molecular weight, $C_8$-$C_{20}$ internal olefin fractions, to produce predominantly aliphatic alcohols from internal olefins at pressures lower than previously used and finally, to outline a method of recovering the product alcohol from non-volatile ruthenium catalyst.

SUMMARY OF THE INVENTION

This invention concerns a method of making alcohols and aldehydes which comprises the steps of contacting a mixture of CO and $H_2$ and terminal or internal olefins with a catalyst system composed of a ruthenium-containing compound dispersed in a low melting quaternary phosphonium or ammonium base or salt and heating said resultant reaction mixture under a pressure of 100 psi or greater at a temperature of at least 50° C. for a sufficient time to produce said alcohols and aldehydes.

DETAILED DESCRIPTION OF THE INVENTION

In the narrower and more preferred practice of this invention, alcohols and aldehydes are prepared concurrently from a synthesis gas mixture of carbon monoxide, hydrogen and olefin substrates by a process comprising the following steps:

(a) Contacting said mixture of carbon monoxide, hydrogen and terminal or internal olefin with a catalyst system composed of a ruthenium-containing compound dispersed in a low melting quaternary phosphonium base or salt of an organic or mineral acid.

(b) Heating said reaction mixture to a temperature of between 100° C. and 220° C., at a pressure of 500 psi or greater, and (c) Isolating said alcohols and aldehydes contained therein.

In order to present the inventive concept in the greatest possible detail to promote its understanding, the following supplementary disclosure is submitted. The basic invention, improved upon here, is practiced as follows:

Catalysts that are suitable in the practice of this invention contain ruthenium. The ruthenium-containing catalyst may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise ruthenium in complex combination with carbon monoxide, hydrogen and olefin substrates. The most effective catalyst is believed to be achieved where ruthenium hydrocarbonyl species are solubilized in a quaternary salt under reaction conditions.

The ruthenium catalyst precursors may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium(II) iodide, anhydrous ruthenium(III) chloride and ruthenium nitrate, or as the salt of a suitable organic carboxylic acid, for example, ruthenium(III) acetate, ruthenium naphthenate, and ruthenium valerate. Ruthenium(III) acetylacetonate is also a suitable catalyst precursor. The ruthenium may furthermore be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium (II) chloride dimer, $[Ru(CO)_3Cl_2]_2$.

Preferred ruthenium-containing compounds include oxides of ruthenium, ruthenium salts of a mineral acid, ruthenium salts of an organic carboxylic acid and ruthenium carbonyl or hydrocarbonyl derivatives. Among the particularly preferred are ruthenium(IV) dioxide hydrate, ruthenium(III) acetylacetonate, and triruthenium dodecacarbonyl. The usefulness of these ruthenium precursors for alcohol and aldehyde synthesis is illustrated by the accompanying Examples I–XXIV.

The ruthenium-containing compound is, prior to its catalytic use in making alcohols and aldehydes, first dispersed in a low melting quaternary phosphonium or ammonium base or salt.

The quaternary phosphonium or ammonium base or salt should be relatively low melting, that is, melt at a temperature less than about the temperature of reaction necessary for making said alcohols and aldehydes. Usually the quaternary compound has a melting point less than about 180° C., and most often has a melting point less than 150° C.

The addition of the quaternary phosphonium or ammonium base or salt to the ruthenium-containing compounds described supra ensures the following improvements in olefin hydroformylation performance;

(1) Improved yields of desired alcohol plus aldehyde product.

(2) Less by-product hydrocarbon formation.

(3) Ease of separation of the ruthenium catalyst from the alcohol and aldehyde products.

(4) Maintained activity for the ruthenium catalyst during multiple recycling experiments.

Illustrative of these improvements are the accompanying examples, particularly Example I and comparative Example II, as well as the ruthenium catalyst recycle experiments of Example IV, VII, and VIII.

Suitable quaternary phosphonium salts for the practice of this invention have the formula:

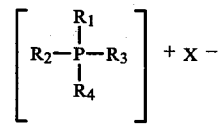

where $R_1$, $R_2$, $R_3$ and $R_4$ are organic radicals, particularly alkyl, aryl or alkaryl radicals bonded to the phosphorous atom, and X is an anionic species. The organic radicals particularly useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, and iodides, are also satisfactory in this instance. Also useful are the corresponding quaternary ammonium bases and salts in the above series of compounds.

Equally useful are the phosphonium and ammonium salts containing phosphorus or nitrogen bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus or nitrogen atom through the aryl function.

Illustrative examples of suitable quaternary phosphonium and ammonium bases and salts include tetrabutyl phosphonium bromide, heptyltriphenylphosphonium bromide, tetrabutylphosphonium iodide, tetrabutylphosphonium chloride, tetrabutylphosphonium nitrate, tetrabutylphosphonium hydroxide, tetrabutylphosphonium chromate, tetrabutylphosphonium tetrafluoroborate, tetrabutylphosphonium acetate, tetrabutylammonium bromide, tetraheptylammonium chloride, tetramethylammonium fluoride, tetramethylammonium hydroxide, pentahydrate, and n-dodecyltriphenylphosphonium bromide, hexadecyltri-n-butylphosphonium bromide, n-dodecyltributylphosphonium bromide, ethyltriphenylphosphonium iodide, benzyl trimethylammonium hydroxide and trimethyldodecylammonium bromide. Tables I and II provide evidence of the effectiveness of these quaternary ammonium and phosphonium salts and bases when in combination with ruthenium(IV) oxide, hydrate, triruthenium dodecacarbonyl and ruthenium(III) acetyl acetonate.

Also suitable in the practice of this invention are N-heterocyclic salts, particularly N-heterocyclic halide salts such as N-ethylquinolinium iodide and N-methylquinolinium bromide.

The preferred quaternary salts are generally the tetralkylphosphonium salts containing alkyl groups having 1–16 carbon atoms, such as methyl, ethyl, butyl, dodecyl and hexadecyl. Preferred tetrabutylphosphonium salts or bases include the bromide, chloride, iodide, acetate and chromate salts and hydroxide base. Tetrabutylphosphonium salts, such as tetrabutylphosphonium bromide, are most preferred for the practice of this invention.

The olefins employed in the practice of this invention include internal and terminal olefins containing two to thirty carbon atoms and mixtures of the same. Examples of suitable olefins include straight-chain terminal olefins such as propylene, 1-butene, 1-octene, 1-decene, 1-dodecene, 1-tetradecene, and 1-hexadecene. Also suitable are branched-chain, terminal olefins such as 3-methyl-1-pentene, 4-methyl-1-hexene, 3,3-dimethyl-1-butene and 3,4-dimethyl-1-hexene, linear and branched, internal olefins are also suitable substrates for this hydroformylation. Examples include 2-octene, 3-octene, 4-octene, mixed internal octenes, mixed internal decenes, mixed internal dodecenes as well as 2-pentene, 3-hexene, 5-decene, 2-decene, 2-dodecene, and 5-methyl-2-hexene. Cyclic olefins like cyclohexene, cyclopentene, cycloheptene and their branched derivatives such as 1-methylcyclohexene and 2-ethylcyclopentene are also useful in the practice of this invention.

Particularly preferred are straight-chain terminal olefins such as propylene, 1-butene, 1-octene, 1-decene and 1-dodecene, as well as linear internal olefins such as 2-octene, mixed internal octenes, mixed internal undecenes and mixed internal $C_{13}$-$C_{14}$ olefins, as well as terminal, internal olefin mixtures thereof.

The quantity of ruthenium catalyst (exclusive of quaternary salt) employed in the instant invention is not critical and may vary over a wide range. In general, the novel process is desirably conducted in the presence of a catalytically effective quantity of the active ruthenium species and quaternary phosphonium or ammonium salt or base which gives the desired products in reasonable yields. The reaction proceeds when employing as little as about $1\times10^{-6}$ weight percent, and even lesser amounts, of ruthenium together with about $1\times10^{-6}$ weight percent of quaternary phosphonium or ammonium salt or base, basis the total weight of the reaction mixture. The upper concentration is dictated by a variety of factors including catalyst cost, partial pressures of carbon monoxide and hydrogen, operating temperature etc. A ruthenium catalyst concentration of from about $1\times10^{-5}$ to about 30 weight percent ruthenium in conjunction with a low melting quaternary phosphonium or ammonium salt or base concentration of from about 0.1 to about 80 weight percent, based on the total weight of reaction mixture is generally desirable in the practice of this invention. The preferred ruthenium to low melting quaternary phosphonium or ammonium salt or base atomic ratio is from about 0.01 to about 10.

The temperature range which can usefully be employed in these syntheses is a variable dependent upon other experimental factors, including the pressure, the concentration and the choice of the particular species of ruthenium catalyst among other things. The range of operability is from about 50° to 350° C. when superatmospheric pressures of syngas are employed. A narrow range of 100°-220° C. represents the preferred temperature range.

Superatmospheric pressures of 100 psi or greater lead to substantial yields of alcohols and aldehydes by the process of this invention. A preferred operating range is above 500 psi and pressures above 3000 psi also provide useful yields of desired alcohols.

The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may or may not undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

In all these syntheses, the amount of carbon monoxide and hydrogen present in the reaction mixture should be sufficient to at least satisfy the stoichiometry of the desired oxonation reaction.

The major by-product of these alcohol and aldehyde syntheses are commonly alkanes, isomerized olefins, and aldols, formed both through condensations with the product aldehydes, and in some cases, from subsequent denydration and reduction of the initially formed aldol.

The aldehyde and alcohol products may be readily separated from the ruthenium-catalyst-containing crude product mixture by conventional means, eg. by fractional distillation in vacuo. The by-products identified supra may also be isolated by conventional means, or they may be recycled with the ruthenium catalysts.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alcohol product, and said material may be recovered by methods well known in the art, such as distillation, fractionation, extraction and the like. A fraction rich in ruthenium catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

Having described the inventive process, the following examples are submitted to supply specific and illustrative embodiments:

The synthesis of linear and branched nonanols from a 2-octene fraction via ruthenium melt catalysis wherein the catalyst precursor is ruthenium(IV) oxide dispersed in tetrabutylphosphonium bromide (m.p. 100° C.), is demonstrated in Example I.

EXAMPLE I

Ruthenium (IV) oxide hydrate (1.15 g, 6.0 mmole) was dispersed in tetrabutylphosphonium bromide (20.0 g, 58.9 mmole), and diluted with 2-octene (22.4 g, 200 mmole) and transferred in a glass liner, under $N_2$ purge, to an 850 ml capacity pressure reactor equipped with heating and means of agitation. The reactor was sealed, flushed with $CO/H_2$ and pressured to 1200 psi with $CO/H_2$ (1:2). The mixture was heated to 180° C. with rocking, held at temperature for six hours and then allowed to cool.

Upon reaching ambient temperature, the reactor pressure (790 psi) was noted, a typical gas sample taken, and the excess gas removed. The deep-red liquid product (48.3 g) was analyzed by glc and Karl Fischer titration.

Analysis of a typical liquid sample showed the following composition:
33.9 wt. % 1-nonanol
29.7 wt. % 2-methyloctanol
6.1 wt. % 2-ethylheptanol
3.8 wt. % 1-nonanal
1.6 wt. % branched $C_9$ aldehydes
9.1 wt. % n-octane
1.9 wt. % octenes
0.6 wt. % water
Analysis of typical gas samples showed the presence of:
53 wt. % Hydrogen
26 wt. % Carbon monoxide
20 wt. % Carbon dioxide
Estimated conversion of octene charge=98%
Estimated total yield of $C_9$ alcohols plus aldehydes=72 mole%

COMPARATIVE EXAMPLE II

This example shows the poorer performance for the ruthenium catalyst in the absence of a quaternary phosphonium salt.

A mixture of ruthenium(IV) oxide, hydrate (1.15 g, 6.0 mmole) and 2-octene (22.4 g, 200 mmole) was transferred, in a glass liner under $N_2$ purge, to an 850 ml capacity pressure reactor equipped with heating and means of agitation. As in Example I, the reactor was sealed, flushed with $CO/H_2$ and pressured to 1200 psi with $CO/H_2$ (1:2). The mixture was heated to 180° C. with rocking, held at temperature for 6 hours, and then allowed to cool.

Upon reaching ambient temperature, the reactor pressure (950 psi) was noted, a typical off-gas sample taken, and the excess gas removed. The yellow liquid (32 ml) plus orange solids were weighed (27.5 g total) and analyzed by glc and Karl Fischer titration.

Analysis of a typical liquid sample shows the following composition:
26.5 wt. % 1-nonanol
11.8 wt. % 2-methyloctanol
2.3 wt. % 2-ethyl heptanol
47.7 wt. % octane
0.1% unreacted octenes
Estimated conversion of octene charge 98%
Estimated total yield of $C_9$ alcohols plus aldehydes=37 mole%

In comparing these results with those of Example I it may be noted that:

(a) The estimated total yield of nonanol plus nonanal products is higher in Example I, with added quaternary phosphonium salt, tetrabutylphosphonium bromide (yield 72 mole % versus 37 mole % in comparative Example II).

(b) The production of by-product hydrocarbon, in this case octane, is lower in Example I, with the added tetrabutylphosphonium bromide (eg. octane concentration in the product mix is 9.1 wt.% versus 47.7 wt.% in Example II).

In the following examples III–VIII a variety of other internal and alpha olefin substrates, particularly mixed internal octenes, mixed internal undecenes, $C_{13}$–$C_{14}$ internal olefin fractions and 1-decene are used for oxonation to the corresponding aliphatic oxo alcohols and aldehydes.

EXAMPLE III

A dispersion of ruthenium(IV) oxide (0.57 g, 3.0 mmole) in tetrabutylphosphonium bromide (10.0 g, 29.5 mmole) was diluted with 18.2 g of a mixed $C_{13}$–$C_{14}$ internal olefin fraction (ca. 100 mmole) and transferred in a glass liner under $N_2$ purge, to an 850 ml capacity pressure reactor equipped with heating and means of agitation. The reactor was sealed, flushed with $CO/H_2$ and pressured to 1200 psi with $CO/H_2$ (1:2). The mixture was heated to 180° C. with rocking, held at temperature for 6 hours and then allowed to cool.

Upon reaching ambient temperature, the reactor pressure (1100 psi) was noted, a typical gas sample taken, and the excess gas removed. The liquid product (32.1 g) was analyzed by glc and Karl Fischer titration.

Analysis of a typical sample showed the following composition:
16.5 wt. % 1-tetradecanol
31.6 wt. % branched $C_{14}$ alcohols
10.8 wt. % 1-pentadecanol
24.4 wt. % branched $C_{15}$ alcohols
6.1 wt. % tridecane
6.1 wt. % tetradecane
0.1 wt. % unreacted $C_{13}$–$C_{14}$ internal olefins
Estimated conversion of $C_{13}$–$C_{14}$ internal olefins 98%
Estimated yield of $C_{14}$–$C_{15}$ alcohols=82 mole%

EXAMPLE IV

A dispersion of ruthenium(IV) oxide hydrate (79 mmole) in tetrabutylphosphonium bromide (250 g, 737 mmole) was diluted with $C_{11}$ mixed internal olefin (1540 g, 10 mole) and transferred to a one gallon capacity pressure reactor equipped with heating and means of agitation. The reactor was sealed, flushed with $CO/H_2$ and pressured to 1200 psi with $CO/H_2$ (1:2). The mixture was heated to 180° C. with stirring, held at temperature for 7 hours and then allowed to cool. During the course of the reaction, the vessel was repressured several times to 1800 psi with $CO/H_2$ (1:2).

Upon reaching ambient temperature, a typical off-gas sample was taken and the excess gas removed. The dark red liquid product (2041 g) was analyzed by glc.

Analysis of a typical liquid sample was as follows:
19.8 wt. % 1-dodecanol
21.1 wt. % 2-methyl undecanol
19.8 wt. % 2-ethyldecanol
0.5 wt. % dodecanal
16.9 wt. % undecane
5.1 wt. % unreacted undecenes Analysis of typical gas samples showed the presence of:
51.8 wt. % hydrogen
14.6 wt. % carbon monoxide
28.2 wt. % carbon dioxide
Estimated conversion of $C_{11}$ internal olefin charge = 92.7%
Estimated total yield of $C_{12}$ alcohols plus aldehydes = 65.9%

The crude liquid product was recovered from the reactor and weighed (2041 g). The weight gain was 236 g. A portion of this liquid product (1694 g) was subject to vacuum distillation. Liquid distillate fractions were recovered as water-white liquids. Their combined weight was 706 g. A typical composition for a distillate fraction having a B. P. range 21°–106° C. was as follows:
5.4 wt. % 1-dodecanol
11.7 wt. % 2-methyl undecanol
14.7 wt. % 2-ethyldecanol
0.6 wt. % 1-dodecanal
2.8 wt. % branched aldehydes
34.1 wt. % undecane/undecene The pot residue (988 g) was recovered as a deep red liquid which contained ruthenium carbonyl species, tetrabutylphosphonium bromide, $C_{12}$ alcohols and some heavier fractions.

EXAMPLE V

A mixture of ruthenium(IV) oxide, hydrate (82 mmole), 1-decene (1500 g, 10.71 mole) and tetrabutylphosphonium bromide (250 g, 0.737 mole) was added to a one gallon capacity pressure reactor equipped with heating and means of agitation. The reactor was sealed, flushed with $CO/H_2$ and pressured to 1200 psi with $CO/H_2$ (1:2). The mixture was heated to 180° C. and agitation was started. At temperature the reactor was connected to a surge tank containing $CO/H_2$ (1:2), and the pressure in the reactor raised to 2200 psi. The mixture was held under 2200 psi at 180° C. for 23 hours and then allowed to cool.

Upon reaching ambient temperature, a typical gas sample was taken and the excess gas removed. The deep-red liquid product (2058 g) was analyzed by glc.

Analysis of a typical liquid sample showed the following composition:
49.9 wt. % 1-undecanol
24.0 wt. % 2-methyldecanol
4.8 wt. % 2-ethylnonanol
12.6 wt. % decane Analysis of typical gas samples showed the presence of:
47.8 wt. % hydrogen
22.3 wt. % carbon monoxide
21.2 wt. % carbon dioxide
Estimated conversion of 1-decene = 100%
Estimated total yield of $C_{11}$ alcohols plus aldehydes = 77.2%

EXAMPLE VI

A mixture of ruthenium(IV) oxide, hydrate (1.5 mmole) in tetrabutylphosphonium bromide (5.0 g, 11.7 mmole) was diluted with $C_{11}$ mixed internal olefin (22.8 g, 150 mmole) and 1-tetradecanol (8.5 g, 40.0 mmole) and transferred in a glass-liner, under $N_2$ purge, to a 300 ml capacity pressure reactor equipped with heating and means of agitation. The reactor was sealed, flushed with $CO/H_2$ and pressured to 1200 psi with $CO/H_2$ (1:2). The mixture was heated to 180° C. with rocking, held at temperature for 4 hours and then allowed to cool.

Upon reaching ambient temperature, the reactor pressure (700 psi) was noted, a typical gas sample taken, and the excess gas removed. The dark brown product is analyzed by glc.

Analysis of a typical liquid sample showed the following composition:
8.8 wt. % 1-dodecanol
9.1 wt. % 2-methylundecanol
7.5 wt. % 2-ethyldecanol
1.2 wt. % 1-dodecanal
10.5 wt. % n-undecane
20.1 wt. % unreacted undecenes
20.7 wt. % 1-tetradecanol
Analysis of typical gas samples showed the presence of:
55.7 wt. % hydrogen
31.6 wt. % carbon monoxide
10.9 wt. % carbon dioxide
Estimated conversion of undecene charge = 70.5%
Estimated yield of $C_{12}$-alcohols plus aldehydes = 52.7%

EXAMPLE VII

A solution (2821 g) containing the pot residual (35.0%) from Example IV and a $C_{11}$ mixed internal olefin (65.0%) is combined and analyzed for ruthenium (1805 μg/ml). The solution was pumped into a 1-liter continuous unit until it was filled. The unit was then heated slowly to 180° C. under 1900 psi of $CO/H_2$ (1:2). The solution was then pumped into the continuous unit at a rate of 50 g/hr. After 5 hours the unit reached steady state conditions. Typical gas samples were taken. Samples of the deep red liquid product were collected and analyzed by glc.

Analysis of a typical liquid sample, once the reactor reached steady state conditions, was as follows:
12.5 wt. % 1-dodecanol
12.3 wt. % 2-methylundecanol
10.3 wt. % 2-ethyldecanol
4.3 wt. % 1-dodecanal
9.2 wt. % branched $C_{12}$ aldehydes.
7.9 wt. % undecane
23.6 wt. % unreacted undecenes Analysis of typical gas samples showed the presence of:
62.0 wt. % hydrogen
29.8 wt. % carbon monoxide
5.8 wt. % carbon dioxide
Estimated conversion of undecene charge = 76.3%

Estimated total yield of $C_{12}$ alcohols plus aldehydes = 63.9%

EXAMPLE VIII

A solution containing the pot residual (35.0%) from Example IV and a $C_{11}$-internal olefin fraction (65.0%) is combined and analyzed for ruthenium (1805 μg/ml) as in Example VII. The solution is pumped (75 g/hr) into a fluid, 1-liter continuous unit kept at 220° C. under $CO/H_2$ (1:2) pressure of 1900 psi. After 3 hours, the unit reached steady state conditions. Typical gas samples were taken. Samples of the deep red liquid product were collected and analyzed by glc.

Analysis of a typical liquid sample once the reactor reaches steady state conditions was as follows:
18.6 wt. % 1-dodecanol
25.6 wt. % 2-methyl undecanol
24.2 wt. % 2-ethyldecanol
0.1 wt. % dodecanal
0.7 wt. % branched $C_{12}$ aldehydes.
14.2 wt. % undecane
3.6 wt. % unreacted undecenes
Analysis of typical gas samples showed the presence of:
55.0 wt. % hydrogen
35.4 wt. % carbon monoxide
4.2 wt. % carbon dioxide Estimated conversion of octene charge = 96.4%
Estimated total yield of $C_{12}$ alcohols/aldehydes = 71.6%

Table I illustrates the effect of employing different quaternary phosphonium salts coupled with different ruthenium sources. Starting with mixed internal octenes, yields of nonanols plus nonanals exceed 80 mole % for the $RuO_2$-$C_{16}H_{33}Bu_3Br$ and $RuO_2$-$Bu_4PI$ combinations (see Example IX and XIII) Linearity of the $C_9$ alcohol product is 69% for the ruthenium(IV) oxide-tetrabutylphosphonium acetate couple (Example XVI).

TABLE I

HYDROFORMYLATION OF INTERNAL OCTENES

| EXAMPLE | RUTHENIUM SOURCE | REACTION MEDIA[a] | LIQUID PRODUCT COMPOSITION (%) | | | | NONANOLS BRANCHED | | | OCTENE CONV (%) | NONANOLS + NONANALS YIELD (%) |
|---------|------------------|-------------------|---------|--------|---------|--------|---------|---------|---------|---------|---------|
| | | | OCTENES | OCTANE | NONANALS | | | | | | |
| | | | | | BRANCH | LINEAR | 2-Et | 2-Me | LINEAR | | |
| IX | $RuO_2.xH_2O$ | $C_{16}H_{33}Bu_3PBr$ | 0.1 | 12.2 | 0.2 | 0.3 | 10.6 | 34.5 | 35.0 | 99 | 81 |
| X | " | $C_7H_{15}Ph_3PBr$ | 0.1 | 15.0 | 0.3 | 0.2 | 9.9 | 32.6 | 34.2 | 99 | 74 |
| XI | " | $C_{12}H_{25}Ph_3PBr$ | 0.1 | 13.4 | 0.1 | 0.3 | 9.9 | 32.4 | 33.1 | 99 | 74 |
| XII | " | $Bu_4PBr$ | 0.2 | 14.2 | 0.3 | 0.2 | 9.8 | 32.9 | 32.1 | 99 | 76 |
| XIII | " | $Bu_4PI$ | 0.4 | 9.8 | 1.2 | 0.1 | 10.9 | 34.4 | 35.3 | 99 | 83 |
| XIV | " | $EtPh_3PI$ | 8.3 | 13.8 | 9.9 | 2.4 | 4.9 | 21.9 | 26.5 | 90 | 68 |
| XV | " | $Bu_4PCl$ | 0.1 | 10.0 | 0.2 | 0.3 | 10.0 | 33.0 | 34.4 | 99 | 76 |
| XVI | " | $Bu_4POAc$ | 41.4 | 5.9 | 1.9 | 0.3 | 2.1 | 9.1 | 24.3 | 54 | 59 |
| XVII | $Ru_3(CO)_{12}$ | $Bu_4PBr$[b] | 0.1 | 18.2 | 0.4 | 0.4 | 9.4 | 30.3 | 28.9 | 99 | 66 |
| XVIII | $Ru(acac)_3$ | $Bu_4PBr$[b] | 0.4 | 14.8 | 0.3 | 0.7 | 10.4 | 30.8 | 27.5 | 99 | 66 |

[a]Typical reaction charge: Ru, 3.0 mmole; quaternary phosphonium salt, 5.0 g; mixed internal octenes, 100 mmole.
Typical run conditions: 180° C., 1200 psi $CO/H_2$ (1:2) initial pressure, 4 hours
[b]Typical reaction charge: Ru, 6.0 mmole; $Bu_4PBr$, 20.0 g; octenes, 200 mmole.

Table II illustrates the case of ruthenium(IV) oxide, hydrate dispersed in different quaternary ammonium salts such as di(octadecyl)dimethylammonium chloride, tetrabutylammonium bromide and tetraheptylammonium chloride (Examples XIX to XXI), as well as use of N-heterocyclic salts such as N-ethylquinolinium iodide (Example XXV).

TABLE II

HYDROFORMYLATION OF INTERNAL OCTENES

| EXAMPLE | RUTHENIUM SOURCE | REACTION MEDIA[a] | LIQUID PRODUCT COMPOSITION | | | | ←NONANOLS→ | | |
|---------|------------------|-------------------|---------|--------|---------|---------|---------|---------|---------|
| | | | OCTENES | OCTANE | ←NONANALS→ | | ←BRANCHED→ | | |
| | | | | | BRANCH | LINEAR | 2-Et | 2-Me | LINEAR |
| XIX | $RuO_x.xH_2O$ | $(C_7H_{15})_4NCl$ | 5.4 | 11.0 | 4.0 | 0.7 | 5.1 | 19.4 | 22.5 |
| XX | " | $Bu_4NBr$ | 11.9 | 0.2 | 0.1 | 0.9 | 6.0 | 23.9 | 27.6 |
| XXI | " | $(C_{18}H_{37})_2Me_2NCl$ | 0.1 | 5.6 | 1.4 | 0.2 | 8.8 | 25.7 | 21.5 |
| XXII | " | $Me_4NF$ [d]{ | 32.3 | 59.8 | | | | | |
| | | | | | 0.5 | 0.1 | 0.1 | | 0.3 |
| | | | 0.5 | 2.3 | | | | | |
| XXIII | " | $Me_4NOAc$ [d]{ | 81.2 | | | 0.5 | | | |
| | | | | 10.0 | 0.6 | | | 0.1 | 0.1 |
| | | | 32.3 | | | 18.5 | | | |
| XXIV | " | $BzMe_3NOH$[c] [d]{ | 40.0 | 2.2 | 4.3 | 4.6 | 0.2 | 0.2 | 0.8 |
| | | | 10.8 | 0.8 | 3.0 | 3.9 | 0.2 | 0.2 | 1.0 |
| XXV | " | Et QUIN. I[b] [d]{ | 90.8 | | | | | | |
| | | | | 2.4 | 0.3 | 0.4 | | | |
| | | | 12.3 | | | | | | |

[a]Typical reaction charge: Ru, 3.0 mmole; quaternary ammonium salt, 5.0 g; octenes, 100 mmole.
Typical run conditions: 180° C.; 1200 psi, $CO/H_2$ (1:2) initial pressure, 4 hours
[b]Et Quin.I, N—ethylquinolinium iodide.
[c]Added as 40% solution in methanol.
[d]A two-phase liquid product.

What is claimed is:
1. An oxo process for preparing alcohols and aldehydes, particularly aliphatic alcohols which comprises the steps of contacting a variety of $C_2$–$C_{30}$ terminal and internal olefins plus synthesis gas with a catalyst system comprising a ruthenium-containing compound derivative dispersed in low-melting quaternary compound selected from the group consisting of quaternary phos- phonium bases, quaternary phosphonium salts, quaternary ammonium bases and quaternary salts and heating resultant reaction mixture under a pressure of 100 psi or greater at a temperature of at least 50° C.

2. The process of claim 1 wherein the ruthenium-containing compound is selected from the group consisting of one or more oxides of ruthenium, ruthenium salts of a mineral acid, ruthenium salts of an organic carboxylic acid and ruthenium carbonyl or hydrocarbonyl derivatives.

3. The process of claim 2 wherein the ruthenium-containing compound is selected from the group consisting of anhydrous ruthenium(IV) dioxide, ruthenium(IV) dioxide hydrate, ruthenium(VIII) tetraoxide, ruthenium(III) trichloride hydrate, ruthenium acetate, ruthenium propionate, ruthenium(III) acetylacetonate and triruthenium dodecacarbonyl.

4. The process of claim 3 wherein said ruthenium containing compound is ruthenium(IV) oxide.

5. The process of claim 3 wherein said ruthenium containing compound is triruthenium dodecacarbonyl.

6. The process of claim 3 wherein said ruthenium containing compound is ruthenium(II) acetylacetonate.

7. The process of claim 1 wherein said quaternary salt or base has a melting point less than about 180° C.

8. The process of claim 1 wherein said quaternary salt is a tetraalkylphosphonium salt.

9. The process of claim 8 wherein said alkyl groups contain 1–16 carbon atoms.

10. The process of claim 9 wherein said tetraalkylphosphonium salt is a tetrabutylphosphonium salt.

11. The process of claim 10 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

12. The process of claim 1 wherein said quaternary is a mixed alkaryl phosphonium quaternary.

13. The process of claim 12 wherein said mixed alkaryl phosphonium quaternary is selected from the group consisting of heptyltriphenylphosphonium bromide, ethyltriphenylphosphonium iodide and dodecyltriphenylphosphonium bromide.

14. The process of claim 1 wherein said quaternary salt is a mixed tetraalkyl phosphonium salt.

15. The process of claim 14 wherein said mixed tetraalkylphosphonium salt is selected from the group consisting of hexadecyltributylphosphonium bromide and heptyltributylphosphonium bromide.

16. The process of claim 1 wherein said quaternary salt is a tetraalkylammonium salt.

17. The process of claim 16 wherein said tetraalkylammonium salt is selected from the group consisting of tetraheptylammonium chloride, tetrabutylammonium bromide, tetramethylammonium fluoride and tetramethylammonium acetate.

18. The process of claim 1 wherein said quaternary salt is selected from the group consisting of mixed alkylammonium salts and mixed alkylbenzylammonium bases.

19. The process of claim 18 wherein said salt is Di(octadecyl)dimethylammonium chloride.

20. The process of claim 18 wherein said base is benzyltrimethylammonium hydroxide.

21. The process of claim 1 wherein the mixture is under a pressure of 500 psi–3000 psi.

22. The process of claim 1 wherein the mixture is heated to a temperature of from 100° C. to about 220° C.

23. The process of claim 1 where the olefins used are terminal olefins.

24. The process of claim 23 wherein the terminal olefins are selected from the group consisting of propylene, 1-octene, 1-decene, 1-dodecene and 1-hexadecene.

25. The process of claim 1 wherein the olefins used are internal olefins.

26. The process of claim 25 wherein the internal olefins are selected from the group consisting of 2-octene, mixed internal octenes, mixed internal $C_{13}$–$C_{14}$ olefins, and mixed internal undecenes.

27. The process of claim 1 wherein the synthesis gas is composed of hydrogen and carbon monoxide in a molar ratio ranging from 1:5 to 5:1.

28. The process of claim 1 where the olefins used are $C_8$–$C_{15}$ terminal and internal olefins.

* * * * *